(12) United States Patent
Yun et al.

(10) Patent No.: US 9,381,352 B2
(45) Date of Patent: Jul. 5, 2016

(54) METHOD FOR STIMULATING LIVING BODY MORE ACCURATELY AND APPARATUS USING THE SAME

(71) Applicant: YBRAIN INC., Seoul (KR)

(72) Inventors: Kyongsik Yun, Seoul (KR); Yongwook Chae, Seoul (KR); Kiwon Lee, Seoul (KR)

(73) Assignee: YBRAIN INC., Seoul (KR)

( * ) Notice: Subject to any disclaimer, the term of this patent is extended or adjusted under 35 U.S.C. 154(b) by 0 days.

(21) Appl. No.: 14/997,649

(22) Filed: Jan. 18, 2016

(65) Prior Publication Data

US 2016/0129249 A1    May 12, 2016

Related U.S. Application Data

(62) Division of application No. 14/026,188, filed on Sep. 13, 2013, now Pat. No. 9,265,943.

(51) Int. Cl.
*A61N 1/36* (2006.01)
*A61B 5/04* (2006.01)

(52) U.S. Cl.
CPC .................. *A61N 1/36014* (2013.01)

(58) Field of Classification Search
CPC ............ A61N 1/36082; A61N 1/0529; A61N 1/36025; A61N 1/36132; A61B 3/024; A61B 5/4064; A61B 5/0006; A61B 5/04004; A61B 2018/00839
See application file for complete search history.

(56) References Cited

U.S. PATENT DOCUMENTS

| | | | |
|---|---|---|---|
| 7,460,903 B2 | 12/2008 | Pineda et al. | |
| 2005/0021103 A1* | 1/2005 | DiLorenzo | A61N 1/3605 607/45 |
| 2005/0124848 A1* | 6/2005 | Holzner | A61B 5/04008 600/9 |
| 2007/0073355 A1 | 3/2007 | Dilorenzo | |
| 2011/0066586 A1 | 3/2011 | Sabel et al. | |
| 2012/0165633 A1 | 6/2012 | Khair | |
| 2014/0180361 A1 | 6/2014 | Burdick et al. | |

* cited by examiner

*Primary Examiner* — Christopher D Koharski
*Assistant Examiner* — Natasha Patel
(74) *Attorney, Agent, or Firm* — Hauptman Ham, LLP

(57) ABSTRACT

An apparatus for more accurately stimulating a living body comprises: a stimulation unit configured to apply a bio-stimulation signal in vicinity to a living body, the bio-stimulation signal being composed of pieces of time-series data having a specific frequency; and a control unit configured to derive bio-stimulation information required to achieve targeted bio-information using time space data indicative of bio-responses interacting at a plurality of different positions in response to the bio-stimulation signal, and derive a relation between the bio-stimulation signal and the bio-responses, and control the stimulation unit to apply the bio-stimulation signal in response to the derived bio-stimulation information. The relation is configured to set the bio-stimulation information as variables in an X matrix (m, t), set the bio-response information as variables in a Y matrix (n, t), and derive an A matrix (n, m) satisfying Y=AX.

4 Claims, 4 Drawing Sheets

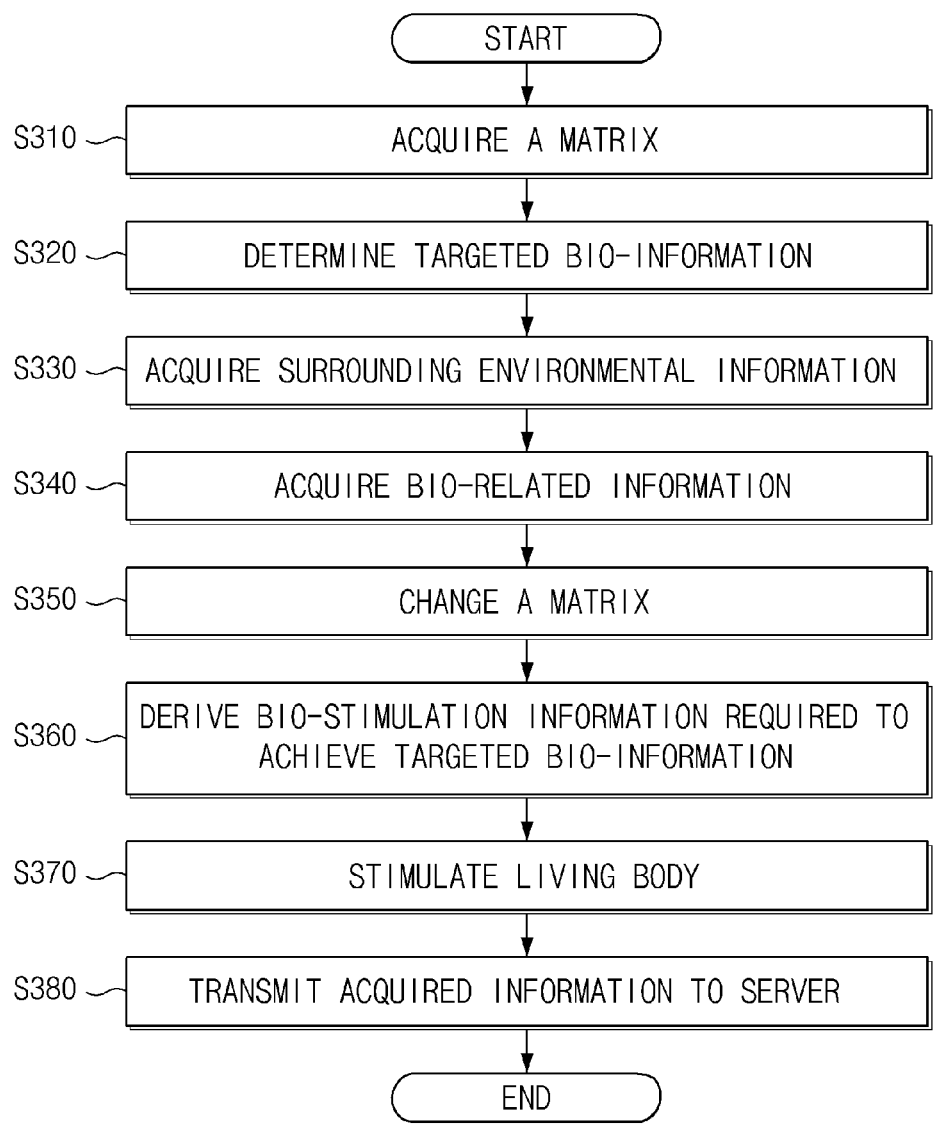

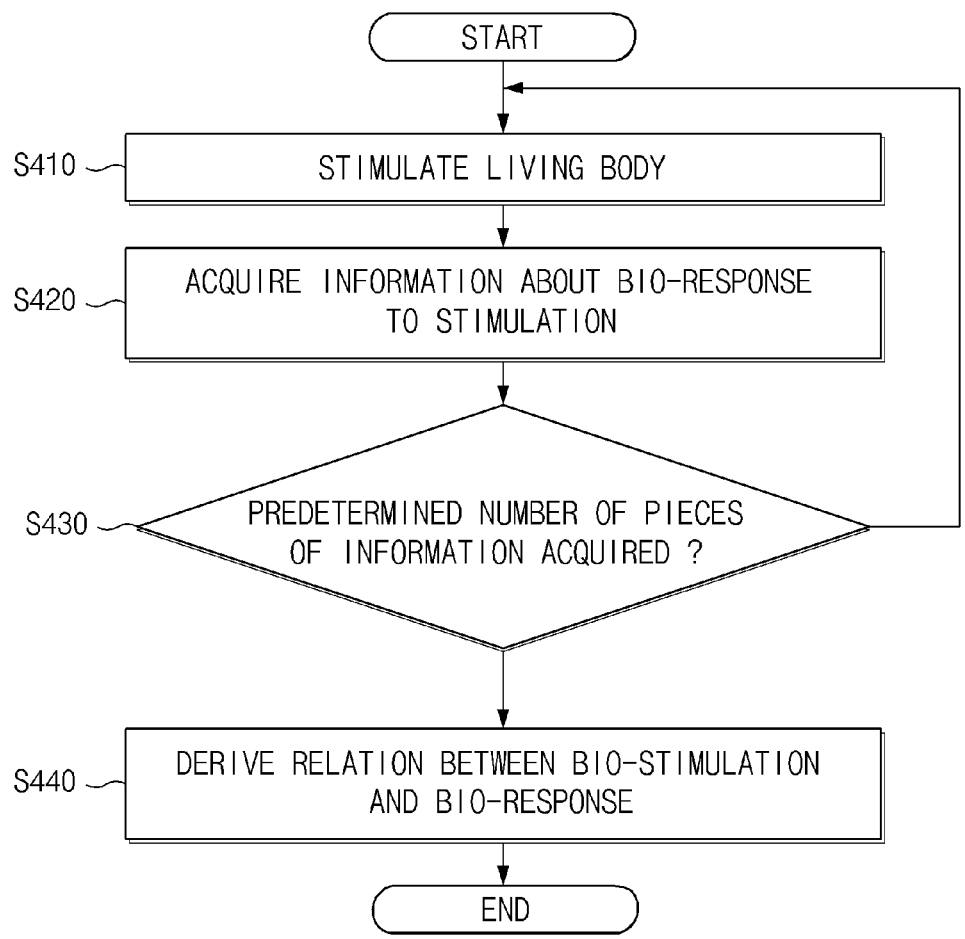

METHOD FOR STIMULATING LIVING BODY MORE ACCURATELY AND APPARATUS USING THE SAME

BACKGROUND OF THE INVENTION

1. Field of the Invention

The present invention relates, in general, to a method of more accurately stimulating a living body and an apparatus using the method and, more particularly, to a method that is capable of more accurately stimulating a living body by deriving a systematic algorithm between bio-related measurement information and stimulation information and to an apparatus using the method.

2. Description of the Related Art

Methods of stimulating a specific portion of a brain are mainly classified into invasive stimulation methods and non-invasive stimulation methods.

Generally, such an invasive stimulation method is a method of exactly installing an electrode at a specific target position via surgery, applying an electrical signal to the electrode, and then directly stimulating a specific portion of the brain.

The invasive stimulation method is an accurate and effective stimulation method, but has a limitation in that a danger caused by brain surgery may be present, and thus this method is limitedly used only in the case of very serious brain diseases, such as Parkinson's disease.

A non-invasive stimulation method is a method of attaching an electrode to a specific position of the scalp, applying electrical and magnetic signals to the electrode, and stimulating a specific portion of the brain.

Such a non-invasive stimulation method is limited in that it is difficult to exactly stimulate the specific portion of the brain, thus requiring a process of trial and error.

Therefore, the non-invasive stimulation method must include the step of stimulating a specific position of the scalp for a predetermined period of time, the step of determining whether the specific position that is targeted is actually stimulated by using a brain signal measurement device, such as Electroencephalography (EEG) equipment or a functional Magnetic Resonance Imaging (fMRI) scanner, and the step of, if it is determined that the specific position has not been stimulated, changing the position of the electrode, stimulating a new specific position of the scalp, and determining whether the new position is actually stimulated by the repositioned electrode.

That is, the non-invasive stimulation method is problematic in that it requires a process of trial and error, thus repeatedly stimulating inaccurate positions.

In particular, when such inaccurate positions are repeatedly stimulated, the non-invasive stimulation method may not obtain targeted effects or may obtain effects lower than the targeted effects, and may cause a problem in safety because a stimulation time is lengthened.

Such conventional cranial nerve stimulation technology includes U.S. Pat. No. 7,460,903 (entitled "Method and system for a real time adaptive system for effecting changes in cognitive-emotive profiles").

Such a conventional cranial nerve stimulation technology includes the step of acquiring various bioelectric signals required to determine a current psychological state, the step of comparing the current psychological state so as to extract a multi-dimensional cognitive-emotive profile based on the bioelectric signals; mapping the cognitive-emotive profile onto a set of commands; the step of delivering brain stimulation commands to drive therapeutic and non-therapeutic stimulus intervention; and the step of applying a prolonged change to the cognitive-emotive profile.

However, such conventional cranial nerve stimulation technology is problematic in that it is implemented using a method in which acquired information matches a command set in which output information corresponding to input information is preset, thus requiring the above-described process of trial and error so as to create the preset command set.

Further, since the command set used in this way is either created depending on experience rules or created using the mechanism of bio-related information that is academically identified, there is a limitation in that the command set is dependent on incomplete experience rules or limited biological mechanisms, thus causing restrictions in precision and accuracy.

SUMMARY OF THE INVENTION

Accordingly, the present invention has been made keeping in mind the above problems occurring in the prior art, and an object of the present invention is to provide a method of deriving a systematic algorithm between bio-related information and stimulation information, which can make more accurate and safely stimulation upon applying bio-stimulation based on acquired bio-related information.

Another object of the present invention is to provide a method for stimulating a living body and an apparatus using the method, which can minimize a process of trial and error using a systematic algorithm.

A further object of the present invention is to provide a method that is capable of more accurately stimulating a living body by exactly determining a specific target stimulation position using a systematic algorithm, and an apparatus using the method.

In order to accomplish the above objects, the present invention provides a method of more accurately stimulating a living body, including determining targeted bio-information; deriving bio-stimulation information required to achieve the targeted bio-information using complicated time space data indicative of bio-responses interacting at a plurality of different positions in response to bio-stimulation composed of pieces of time-series data having a specific frequency; and applying a stimulation signal to the living body in response to the derived bio-stimulation information.

Preferably, information about bio-responses to the bio-stimulation may be a relation between the bio-stimulation and the bio-response information, the relation being analyzed by performing applying the bio-stimulation; and acquiring information about a bio-response to the applied bio-stimulation.

Preferably, the relation between the bio-stimulation and the bio-response information may be configured to set information about the bio-stimulation as variables in an X matrix (m,t), set the bio-response information as variables in a Y matrix (n,t), derive an A matrix (n,m) satisfying Y=AX, and use the A matrix as the relation between the bio-stimulation and the bio-response information.

Preferably, values in the A matrix may be determined to be mean values of values derived during respective repetitions.

Preferably, values in the A matrix may be derived using a pseudo-inverse method when a plurality of types of bio-stimulation and information about a plurality of bio-responses to the bio-stimulation are acquired.

Further, the present invention provides an apparatus for more accurately stimulating a living body, including a stimulation unit for applying a bio-stimulation signal in close vicinity to a living body; and a control unit for deriving bio-stimulation information required to achieve targeted bio-information using information about a bio-response to bio-stimulation, and controlling the stimulation unit so that the stimulation unit applies the bio-stimulation signal in response to the derived bio-stimulation information.

Preferably, the apparatus may further include an environment sensor for acquiring surrounding environmental information of the living body; and a measurement unit for acquiring bio-related information in close vicinity to the living body, wherein the control unit analyzes a relation between the surrounding environmental information of the living body acquired by the environment sensor and the bio-related information acquired by the measurement unit and uses the relation to derive bio-stimulation information required to achieve the targeted bio-information.

Details of other embodiments are included in the following detailed description and drawings.

BRIEF DESCRIPTION OF THE DRAWINGS

FIG. 3 is a flowchart showing a method for more accurately stimulating a living body according to an embodiment of the present invention; and FIG. 4 is a flowchart showing a method of driving an A matrix according to an embodiment of the present invention.

DESCRIPTION OF THE PREFERRED EMBODIMENTS

The above and other objects, features and advantages of the present invention will be more clearly understood from the following detailed description taken in conjunction with the accompanying drawings. However, the present invention is not limited by the following embodiments and may be implemented in various forms. The present embodiments are configured to merely make the disclosure of the present invention complete and are provided to fully describe the scope of the present invention to those having ordinary knowledge in the art to which the present invention pertains, and the present invention is merely defined by the scope of the accompanying claims. Meanwhile, the terms used in the present specification are intended to describe embodiments and are not intended to limit the scope of the present invention.

Figure 1:
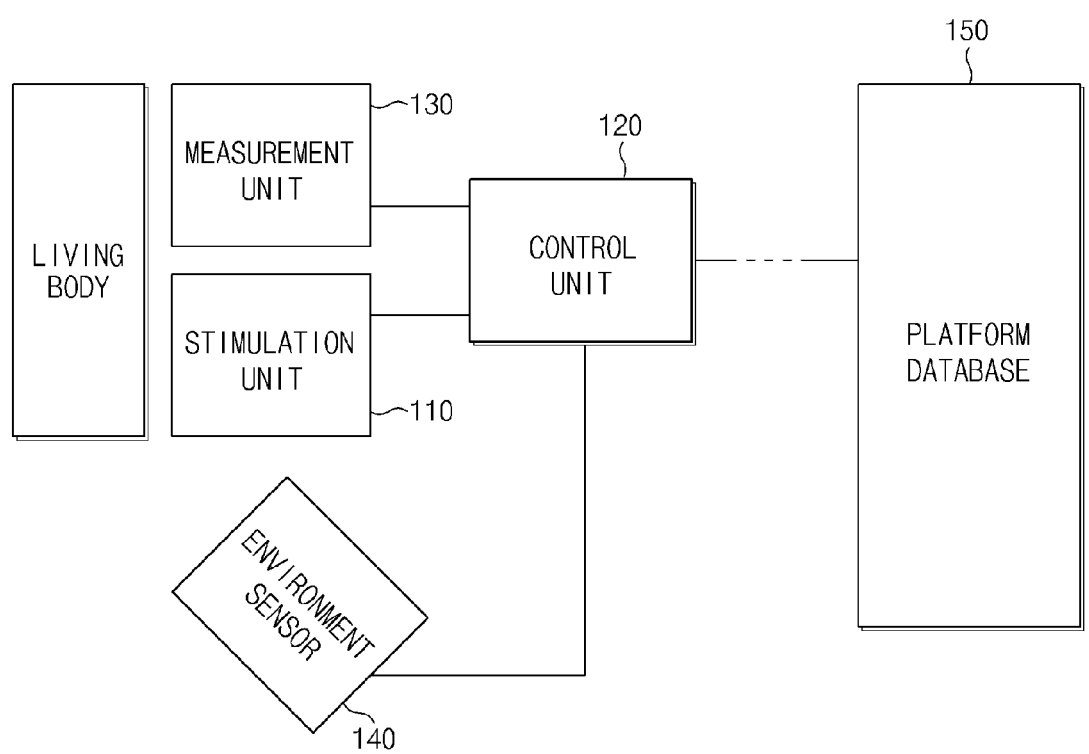
FIG. 1 is a block diagram showing an apparatus for more accurately stimulating a living body according to an embodiment of the present invention.

FIG. 1 is a block diagram showing an apparatus for more accurately stimulating a living body according to an embodiment of the present invention. Referring to FIG. 1, the apparatus for more accurately stimulating a living body according to the embodiment of the present invention includes a stimulation unit 110 for applying a bio-stimulation signal in close vicinity to a living body, and a control unit 120 for deriving bio-stimulation information required to achieve targeted bio-information and controlling the stimulation unit 110 so that it applies the bio-stimulation signal in response to the derived bio-stimulation information.

The stimulation unit 110 applies a bio-stimulation signal capable of causing a bio-response in close vicinity to the living body.

For example, the stimulation unit 110 may use electrical stimulation, magnetic stimulation, photic stimulation, ultrasonic stimulation, etc.

Electrical stimulation may be provided using a scheme for applying Direct Current (DC) stimulation, pulse stimulation, Alternating Current (AC) stimulation, or random noise stimulation through an electrode installed in close vicinity to a living body. Magnetic stimulation may enable a magnetic stimulus to be applied using a coil for generating a magnetic field in close vicinity to a living body. Further, photic stimulation may enable a stimulus to be applied by emitting infrared rays, near-infrared rays, visible rays, or laser light to a living body. Furthermore, ultrasonic stimulation may enable a stimulus to be applied via an ultrasonic transducer or an ultrasound transceiver, which creates an ultrasonic vibration when in contact with the living body.

Preferably, the stimulation unit 110 applies stimulation to the brain among portions of the living body, and may use transcranial direct current stimulation (tDCS), transcranial alternating current stimulation (tACS), transcranial pulsed current stimulation (tPCS), etc.

Further, preferably, the stimulation unit 110 may be configured to be included in a portable headset worn on the head and may be designed to easily apply stimulation to the brain among the portions of the living body.

The apparatus for more accurately stimulating the living body according to the embodiment of the present invention further includes a measurement unit 130 for acquiring bio-related information in close vicinity to the living body.

Preferably, the measurement unit 130 measures the activities of the brain using brain waves, a brain evoked potential, brain activity, magnetoencephalogram, ultrasonic waves, etc.

For example, the measurement unit 130 may be implemented using an Electroencephalogram (EEG) sensor, a near infrared spectrophotometer (or near infrared spectroscopy: NIRS), magnetoencephalography (MEG) equipment, an ultrasound transceiver, or the like.

In an example, the measurement unit 130 is implemented as an electrode attached to the scalp and is capable of measuring the electrical activities of the brain, and the brain wave measurement electrode may be implemented using a capacitive electrode which has conductivity, but has a surface coated with a nonconductive material.

Further, the brain wave measurement electrode may preferably be used in a non-contact manner.

In another example, the measurement unit 130 is implemented as an electrode attached to the scalp and is capable of measuring the magnetic activities of the brain.

In a further example, the measurement unit 130 may measure a brain evoked potential. The brain evoked potential refers to the electrophysiological response of the brain to stimulation, and any of sensible, cognitive, and motional stimuli may be applied as such stimulation.

As detailed examples, the measurement unit 130 may measure EEG from a body to which electrical, magnetic, photic, or ultrasonic stimulation is applied, and may determine the measured EEG to be the brain evoked potential.

In yet another example, the measurement unit 130 may acquire brain activity using a near infrared spectrophotometer (or NIRS) that exploits a light source for radiating light having a specific wavelength, such as near infrared rays, and a light receiving device (photodetector) for analyzing light absorption caused by the activities of the brain.

In this case, the measurement unit 130 may include a plurality of light sources and photodetectors so as to detect the activation of the brain depending on positions at the brain.

In still another example, the measurement unit 130 may be implemented using an ultrasonic coupler and an ultrasonic receiver, or an ultrasound transceiver which is a combination thereof, and may measure the structure of the brain and the activities of blood vessels.

Preferably, the measurement unit 130 may be configured to acquire bio-information using a plurality of electrical, magnetic, photic, or ultrasonic components. According to the configuration of the measurement unit 130, the stimulation unit 110 may be configured to apply bio-stimulation using the plurality of electrical, magnetic, photic, or ultrasonic components.

The control unit 120 derives bio-stimulation information required to achieve targeted bio-information using information about a bio-response to bio-stimulation, and controls the stimulation unit 110 so that it applies a bio-stimulation signal in response to the derived bio-stimulation information.

In accordance with a preferred embodiment of the present invention, the control unit 120 repeatedly performs a procedure for applying bio-stimulation and acquiring information about a bio-response to the applied bio-stimulation, derives a relation between the bio-stimulation and the bio-response information, and uses the relation as the information about the bio-response to the bio-stimulation.

In accordance with another preferred embodiment of the present invention, the control unit 120 sets information about bio-stimulation as variables in an X matrix (m,t), sets information about the bio-response to the bio-stimulation as variables in a Y matrix (n,t), derives an A matrix (n,m) satisfying Y=AX, and uses the derived A matrix as information about the bio-response to the bio-stimulation.

Preferably, m may be the type of stimulation (where identical stimulation at different positions may be regarded as separate stimuli), n may be the type of bio-information (where identical bio-information at different positions may be regarded as pieces of separate bio-information), and t may be the number of repetitions (or the number of stimulation values and bio-information values acquired for a predetermined period of time).

That is, the control unit 120 sets the targeted bio-information as a Y matrix using the derived A matrix, derives an X matrix satisfying Y=AX, and determines bio-stimulation information corresponding to a required type (or a required position) according to the X matrix.

In accordance with the preferred embodiment of the present invention, values in the A matrix are determined to be mean values of values derived during respective repetitions.

Preferably, values in the A matrix are determined in such a way as to limit the type of stimulation (for example, a value is applied only to single stimulation and the remaining values are set to '0'), acquire a base vector of the A matrix using the acquired bio-information, and determine the values in the A matrix to be mean values of values of base vectors obtained by repeating a base vector acquisition procedure.

In accordance with another embodiment of the present invention, values in the A matrix may be obtained using a pseudo-inverse method.

For example, when a plurality of stimulation values and a plurality of bio-information values are repeatedly acquired, a pseudo-inverse matrix may be configured and thereafter values in the A matrix may be obtained.

When there are a number of equations more than a number of unknown values, a method using the pseudo-inverse matrix is used to obtain a least squares solution, and this method may be usefully applied to the present invention.

In the simplest example, a method using a pseudo-inverse matrix is used to obtain the least squares solution when the number of pieces of information about values to be obtained from a quadratic equation is greater than two pairs and then a solution cannot be obtained.

For example, such a method is configured to, if it is assumed that A matrix [a, b] is obtained for X matrix $$\begin{bmatrix} x \\ 1 \end{bmatrix}$$

and for Y matrix [y], obtain a and b values required to minimize error when assuming that values of x are $(x_1, x_2, \ldots, x_i)$ and values of y corresponding thereto are $(y_1, y_2, \ldots, y_i)$.

In an example of the method applied to the present invention, the control unit 120 changes variables in the X matrix as bio-stimulation has changed, and changes variables in the Y matrix as bio-information which is the bio-response to the bio-stimulation has changed, and then a plurality of equations Y=AX are derived. In this case, there may occur a case where the control unit 120 cannot determine the solution of the A matrix to be a single solution due to measurement noise or the like. In this case, the A matrix for minimizing error may be obtained using the pseudo-inverse matrix.

The method using the pseudo-inverse matrix is advantageous in that, even when relations between stimulation values and bio-information values are unclear due to noise or the like, the A matrix for minimizing error may be derived.

More preferably, the control unit 120 may derive and use the A matrix by performing repetitive stimulation and measurement on a single living body via the stimulation unit 110 and the measurement unit 130.

Further, the control unit 120 may derive bio-stimulation information required to achieve targeted bio-information, based on the A matrix derived via stimulation and measurement performed on a plurality of living bodies.

Although, in the above description, for the convenience of description, an object for deriving the A matrix is described as being the apparatus of the present invention to be claimed, the A matrix is not necessarily calculated by the apparatus including both the measurement unit and the stimulation unit, and a case where the A matrix obtained according to the above description is obtained from the outside of the apparatus and is then used may also be included in the scope of the present invention.

The apparatus for more accurately stimulating a living body according to another preferred embodiment of the present invention further includes an environment sensor 140 for acquiring the surrounding environmental information of a living body.

In this case, the control unit 120 analyzes a relation between the surrounding environmental information of the living body acquired by the environment sensor 140 and bio-related information acquired by the measurement unit 110, similarly to a manner in which the relation between the stimulation information and the bio-response information is derived.

Preferably, the surrounding environmental information of the living body acquired by the environment sensor 140 may be used as variables in the X matrix upon deriving the A matrix. Preferably, the environment sensor 140 is a device for measuring temperature, humidity, illuminance, noise, or the like in surrounding environment that may influence bio-signals.

The apparatus for more accurately stimulating a living body according to a further embodiment of the present invention may be configured to transmit acquired information to a platform database (DB) 150 via a communication terminal or its own communication unit.

The platform DB 150 stores the bio-response information, the bio-stimulation information, and the A matrix which is a relation between the bio-response information and the bio-stimulation information, as complicated space-time data.

Preferably, the platform DB 150 stores the bio-response information as frequency variation information over time using a wavelet transform.

Preferably, the platform DB 150 additionally stores analysis results derived using phase synchrony, partial directed coherence (PDC) or granger causality analysis methods.

Further, the platform DB 150 preferably stores surrounding environmental noise and environmental information measured by a gyroscope and an accelerometer, with the noise and the environmental information time-locked to the bio-response information, the bio-stimulation information, and the A matrix which is the relation between the two types of information.

The platform DB 150 may individually map such various types of information to a multi-dimensional space, and store the various types of information so that they may be classified for respective features.

The platform DB 150 has big data storage characteristics, and may have the form of a distributed DB with high update performance, such as a Cassandra DB, or the form of a distributed file system (DFS) with high processing throughput, such as a Hadoop DB. Alternatively, the platform DB 150 may have both the two forms.

Figure 2:
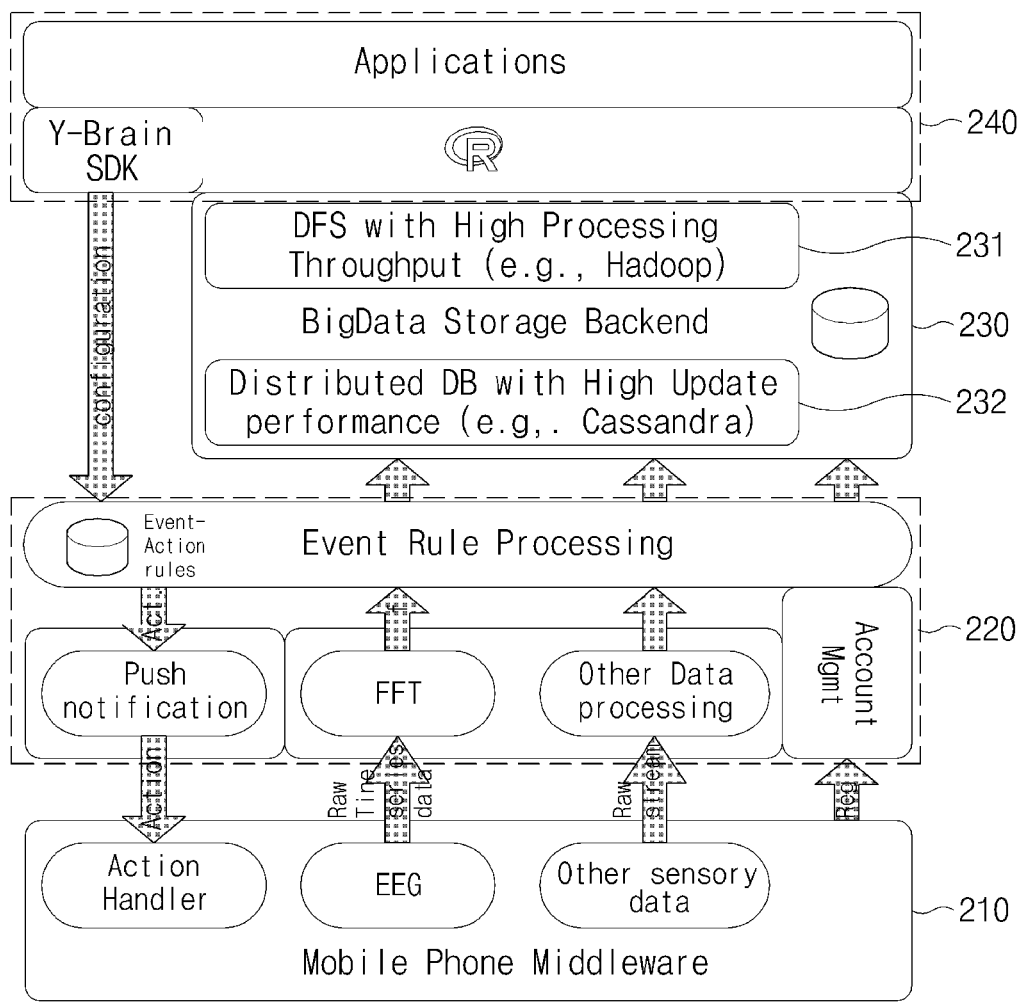
FIG. 2 is a diagram showing the configuration of a system to which the apparatus for more accurately stimulating a living body is applied according to an embodiment of the present invention.

FIG. 2 is a diagram showing the configuration of a system to which the apparatus for more accurately stimulating a living body is applied according to an embodiment of the present invention. Referring to FIG. 2, the system includes the apparatus for more accurately stimulating a living body according to the embodiment of the present invention or a terminal 210 for receiving information from the apparatus, a server 220 for receiving data from the apparatus or the terminal 210 and processing the data, a DB 230 for receiving the data from the server 220 and processing or storing the data, and a second user terminal 240 for requesting data from the server 220.

As described above with reference to FIG. 1, the apparatus or the terminal 210 has bio-stimulation information and bio-response information, and transmits the information to the server 220 through a signal processing unit.

Preferably, the apparatus or the terminal 210 transmits not only bio-stimulation information and bio-response information, but also A matrix data, signal-processed metadata, the location of the apparatus or the terminal, personal information, etc. using various communication methods.

The server 220 transforms or processes the information received from the apparatus or the terminal 210 into a data format that can be processed by the server by performing information processing on the received information based on a preset event-action rule.

The server 220 stores the transformed or processed data in the DB 230.

Preferably, the DB 230 includes a primary DB 231 with a high update speed (for example, the above-described distributed DB [a detailed example: a Cassandra DB]) and a secondary DB 232 having high semantic information extraction performance (for example, the above-described DFS [a detailed example: a Hadoop DB]).

The secondary DB 232 extracts semantic information from the stored DB according to a preset statistical or algorithmic scheme, and stores or processes the extracted semantic information.

The primary DB 231 and the secondary DB 232 may be integrated into a single DB.

The server 220 stores the transformed or processed data in the primary DB 231, and stores some data, which can be stored or deleted or which enables semantic information thereof to be processed according to the type and format of data, in the secondary DB 232.

The server 220 may extract data from the DB 230 and provide the extracted data when the second user terminal 240 requests data.

Preferably, the server 220 may be configured to permit only the access of the second user terminal 240, the apparatus or the terminal 210, which conforms to a program corresponding to a preset scheme (for example, Software Development Kit: SDK or Application Programming Interface: API), with respect to respective attempts to access.

FIG. 3 is a flowchart showing a method of more accurately stimulating a living body according to an embodiment of the present invention. A procedure for performing individual steps shown in FIG. 3 is apparent according to the description made with reference to FIGS. 1 and 2, and thus a detailed description thereof will be omitted.

Referring to FIG. 3, in the method for of more accurately stimulating a living body according to the embodiment of the present invention, the stimulation apparatus performs the step S310 of acquiring an A matrix and the step S320 of determining targeted bio-information.

The stimulation apparatus may first determine targeted bio-information or may first acquire the A matrix. However, the A matrix must be acquired before bio-stimulation information is derived.

The step S310 of acquiring the A matrix may be configured such that the stimulation apparatus acquires the A matrix by repeating the application of stimulation and measurement of response information, or derives the A matrix by acquiring information from the outside, or acquires the A matrix by receiving a completed A matrix.

In accordance with a preferred embodiment of the present invention, the stimulation apparatus may perform the step S330 of acquiring surrounding environmental information, and the step S340 of acquiring bio-related information under the condition of the acquired surrounding environmental information. These steps are required to perform the A matrix change step S350 of further advancing the A matrix, wherein, in this case, the stimulation apparatus must perform the A matrix acquisition step S340 before the A matrix change step S350 is performed.

Thereafter, since the stimulation apparatus acquires the targeted bio-information and the A matrix as information, it performs the step S360 of deriving bio-stimulation information required to achieve targeted bio-information, based on the information, and the step S370 of stimulating the living body based on the derived bio-stimulation information.

Further, the stimulation apparatus according to a predetermined embodiment of the present invention may perform the step S380 of transmitting the acquired information to the server, and such information transmission may be performed at any step.

FIG. 4 is a flowchart showing a method of deriving an A matrix according to an embodiment of the present invention. The procedure for performing individual steps shown in FIG. 4 is apparent by the description made with reference to FIG. 1, and thus a detailed description thereof will be omitted.

Referring to FIG. 4, in the method of deriving an A matrix according to the embodiment of the present invention, an analysis device for deriving an A matrix may sequentially perform the step S410 of stimulating a living body, the step S420 of acquiring information about a bio-response to such stimulation, and the step S440 of deriving an A matrix which is a relation between the bio-stimulation and the bio-response.

Preferably, the analysis device may further perform the step S430 of determining whether a predetermined number of pieces of information have been acquired so as to repeat the step S410 of stimulating the living body and the step S420 of acquiring bio-response information until a predetermined number of pieces of information are accumulated.

Further, preferably, the analysis device may transmit the derived A matrix to the server.

As described above, the present invention is advantageous in that it derives a systematic algorithm between bio-related information and stimulation information, which can make more accurate and safely stimulation upon applying bio-stimulation based on acquired bio-related information.

Further, the present invention is advantageous in that it can minimize a process of trial and error using a systematic algorithm.

Furthermore, the present invention is advantageous in that it can more accurately stimulate a living body by exactly determining a specific target stimulation position.

Although the preferred embodiments and applied embodiments of the present invention have been illustrated and described, those skilled in the art will appreciate that the present invention is not limited by the above-described specific embodiments and applied embodiments and various modifications are possible, without departing from the scope and spirit of the invention as disclosed in the accompanying claims. These modifications should not be understood separately from the technical spirit or prospect of the present invention.

What is claimed is:

1. An apparatus for more accurately stimulating a living body, comprising:

a stimulation unit configured to apply a bio-stimulation signal in vicinity to a living body, the bio-stimulation signal being composed of pieces of time-series data having a specific frequency; and a control unit configured to derive bio-stimulation information required to achieve targeted bio-information using time space data indicative of bio-responses interacting at a plurality of different positions in response to the bio-stimulation signal, and derive a relation between the bio-stimulation signal and the bio-responses, and control the stimulation unit to apply the bio-stimulation signal in response to the derived bio-stimulation information, wherein the relation is configured to set the bio-stimulation information as variables in an X matrix (m, t), set the bio-response information as variables in a Y matrix (n, t), and derive an A matrix (n, m) satisfying Y=AX.

2. The apparatus of claim 1, further comprising:

an environment sensor configured to acquire surrounding environmental information of the living body; and a measurement unit configured to acquire bio-related information in vicinity to the living body, wherein the control unit is configured to analyze a relation between the surrounding environmental information of the living body acquired by the environment sensor and the bio-related information acquired by the measurement unit and use the relation to derive the bio-stimulation information required to achieve the targeted bio-information.

3. The apparatus of claim 1, wherein values in the A matrix are determined to be mean values of values derived during respective repetitions.

4. The apparatus of claim 1, wherein values in the A matrix are derived using a pseudo-inverse method to obtain the least squares solution when a plurality of types of bio-stimulation and information about a plurality of bio-responses to the bio-stimulation are acquired.

* * * * *